US012784900B2

(12) United States Patent
Weyen et al.

(10) Patent No.: US 12,784,900 B2
(45) Date of Patent: Nov. 3, 2026

(54) INVENTORY MANAGEMENT SYSTEMS FOR LINEN AND OTHER ITEMS

(71) Applicant: Sugarloaf River LLC, Bonita Springs, FL (US)

(72) Inventors: Daniel E. Weyen, Cashiers, NC (US); Robert M. Fitzgerald, Cashiers, NC (US)

(73) Assignee: Sugarloaf River LLC, Bonita Springs, FL (US)

( * ) Notice: Subject to any disclaimer, the term of this patent is extended or adjusted under 35 U.S.C. 154(b) by 495 days.

(21) Appl. No.: 18/142,746

(22) Filed: May 3, 2023

(65) Prior Publication Data

US 2023/0360782 A1 Nov. 9, 2023

Related U.S. Application Data

(60) Provisional application No. 63/337,876, filed on May 3, 2022.

(51) Int. Cl.

*G16H 40/20* (2018.01)
*G01G 19/414* (2006.01)
*G01G 19/52* (2006.01)

(52) U.S. Cl.

CPC ........... *G16H 40/20* (2018.01); *G01G 19/414* (2013.01); *G01G 19/52* (2013.01)

(58) Field of Classification Search

CPC ....... G01G 19/52; D06F 95/002; D06F 95/00; G16H 40/20; G06Q 10/087; F24F 11/63
See application file for complete search history.

(56) References Cited

U.S. PATENT DOCUMENTS

| | | | | |
|---|---|---|---|---|
| 1,745,518 A * | 2/1930 | Vance | .................... | A47B 67/04 312/334.44 |
| 6,658,322 B1 | 12/2003 | Frederick et al. | | |
| 6,876,902 B2 | 4/2005 | Nikolich | | |
| 6,975,922 B2 | 12/2005 | Duncan et al. | | |

(Continued)

FOREIGN PATENT DOCUMENTS

| | | |
|---|---|---|
| EP | 0733985 A2 | 6/1997 |
| WO | 2019178031 A1 | 9/2019 |

OTHER PUBLICATIONS

Https://www.arlynscales.com/scale-knowledge/special-weighing-problems-solved-custom-load-cells.

*Primary Examiner* — Shelby A Turner
*Assistant Examiner* — Ibrahim Nagi Shohatee
(74) *Attorney, Agent, or Firm* — Thomas | Horstemeyer, LLP

(57) ABSTRACT

Systems for managing linen inventory that, in various embodiments, comprise a plurality of computerized smart bins that each comprise at least one weight sensor that is adapted to measure a weight of linen items within the respective smart bin. In particular embodiments, each respective smart bin is adapted to weigh items within the respective smart bin, determine a current number of items stored within the respective smart bin based on the measured weight of items within the respective smart bin, and communicate an indication of a number of items that need to be added to, or removed from, the smart bin in order to meet a particular inventory objective. The smart bins may be networked together with each other and/or with other smart devices or other computing devices to facilitate managing items within a facility, such as a healthcare facility.

20 Claims, 10 Drawing Sheets

(56) References Cited

U.S. PATENT DOCUMENTS

| | | | |
|---|---|---|---|
| 7,428,447 B2 | 9/2008 | Stonikas et al. | |
| 7,628,410 B2 | 12/2009 | Fitzgerald et al. | |
| 8,521,620 B2 | 8/2013 | Livingston et al. | |
| 10,032,342 B1 | 7/2018 | Foina | |
| 10,853,764 B2 | 12/2020 | Durkee et al. | |
| 10,939,077 B2 | 3/2021 | Bashkin | |
| 11,137,765 B2 | 10/2021 | Dejarnette et al. | |
| 2013/0218511 A1* | 8/2013 | Mager | G06Q 10/087 702/129 |
| 2015/0088306 A1 | 3/2015 | Varrasso | |
| 2015/0294525 A1 | 10/2015 | Broom et al. | |
| 2018/0121866 A1 | 5/2018 | Higham et al. | |
| 2018/0189720 A1 | 7/2018 | Henderson et al. | |
| 2019/0177012 A1* | 6/2019 | Feiner | B65B 1/46 |
| 2019/0231467 A1 | 8/2019 | Grimsley et al. | |
| 2019/0311322 A1 | 10/2019 | Dejarnette et al. | |
| 2019/0388171 A1 | 12/2019 | Schermeier et al. | |
| 2020/0381107 A1* | 12/2020 | Lowry | G08B 3/10 |
| 2022/0104636 A1* | 4/2022 | Chila | G01G 19/52 |

* cited by examiner

INVENTORY MANAGEMENT SYSTEMS FOR LINEN AND OTHER ITEMS

CROSS REFERENCE TO RELATED APPLICATIONS

This application claims priority from U.S. Provisional Application No. 63/337,876, entitled "Inventory Management Systems for Linen and Other Items," filed May 3, 2022, which is hereby incorporated herein by reference in its entirety.

BACKGROUND

In the current healthcare environment, hospitals face a number of challenges. One such challenge is to remain profitable in light of increasing public pressure to keep healthcare affordable. One way to maintain profitability is to reduce operational costs.

Over the years, hospitals have been able to reduce (or at least stabilize) operational costs in a number of areas. However, the costs associated with providing and laundering hospital linens have proven difficult to control.

One challenge associated with controlling the costs associated with providing and laundering hospital linens is that linens are difficult to track and to inventory within a hospital or other medical facility. As a result, using conventional systems, most hospital administrators have little to no visibility as to how many linens are at different locations within their hospitals, how many linens have been misappropriated by employees and patients, and how many linens have been sent to third-party laundering facilities for cleaning. This results in the loss of linen inventory (e.g., through theft and poor tracking of the inventory) and potential financial losses due to inaccuracies in tracking the amount of laundry processed by third-party laundering facilities.

Accordingly, a need exists to more accurately track linens within a hospital in order to reduce costs associated with providing and maintaining the linens. Such a solution would also be beneficial in helping maintain appropriate linen inventory levels at different locations within a hospital and in monitoring the performance of various hospital workers as they stock the linens.

SUMMARY

A system for managing linen inventory, according to various embodiments, comprises a plurality of computerized smart bins that each comprise: (1) at least one smart bin computer processor; (2) memory that is operatively coupled to the at least one smart bin computer processor; (3) at least one weight sensor that is adapted to measure a weight of linen items within the smart bin, and that is adapted to communicate with the at least one smart bin computer processor; and (4) at least one communications interface for communicating information from the at least one smart bin computer processor to a human user. In particular embodiments, each respective smart bin is adapted to weigh items within the respective smart bin, determine a current number of items stored within the respective smart bin based on the measured weight of items within the respective smart bin, and communicate, via the communications interface, an indication of a number of items that need to be added to, or removed from, the smart bin in order to meet a particular inventory objective.

A system for managing linen inventory, according to various embodiments, comprises a plurality of computerized smart bins that each comprise: (1) at least one smart bin computer processor; (2) memory that is operatively coupled to the at least one smart bin computer processor; (3) at least one linen item sensor that is adapted to determine a quantity of linen items within the respective smart bin; and (4) at least one communications interface for communicating information from the at least one smart bin computer processor to a human user. In various embodiments, each respective smart bin is configured to use the linen item sensor to determine a quantity of linen items within the respective smart bin and communicate, via the communications interface, an indication of a number of items that need to be added to, or removed from, the smart bin in order to meet a particular inventory objective.

A method of managing linen inventory, according to various embodiments, comprises: (1) providing a plurality of computerized smart bins that each comprise: (a) at least one smart bin computer processor; (b) memory that is operatively coupled to the at least one smart bin computer processor; (c) at least one weight sensor that is adapted to measure a weight of linen items within the smart bin, and that is adapted to communicate with the at least one smart bin computer processor; and (d) at least one communications interface for communicating information from the at least one smart bin computer processor to a human user; and (2) using the plurality of smart bins to manage the inventory of linen items within a facility. In particular embodiments, each respective smart bin is adapted to weigh items within the respective smart bin, determine a current number of items stored within the respective smart bin based on the measured weight of items within the respective smart bin, and communicate, via the communications interface, an indication of a number of items that need to be added to, or removed from, the smart bin in order to meet a particular inventory objective.

BRIEF DESCRIPTION OF THE DRAWINGS

Various embodiments of a system and method for managing the inventory of items such as linen items are described below. In the course of this description, reference will be made to the accompanying drawings, which are not necessarily drawn to scale, and wherein.

Like reference numbers and designations in the various drawings indicate like elements.

DETAILED DESCRIPTION

Various embodiments now will be described more fully hereinafter with reference to the accompanying drawings. It should be understood that the invention may be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Overview

A linen inventory management system according to various embodiments addresses the above issues with a combination of unique technologies. First, the system includes a network of smart bins that may, for example, have integrated scales and that are configured for using data from the scales to at least substantially continuously (e.g., continuously) monitor the inventory of linens within the bins. Second, the system may include a network of smart carts that are used to: (1) transport the smart bins as hospital workers use the carts to stock the hospital with linens; and (2) communicate with hospital workers as they stock the linens in order to improve the workers' performance and assure that linen inventory levels are maintained properly. Third, the system may be configured for using the smart bins and smart carts to track linen inventory throughout the hospital (e.g., at least substantially in real time (e.g., in real time), via a suitable graphical user interface), and to thereby track the performance of hospital stocking personnel. Each of these various aspects of the present disclosure is discussed in greater detail below.

Smart Bins

General Structure

Figure 2:
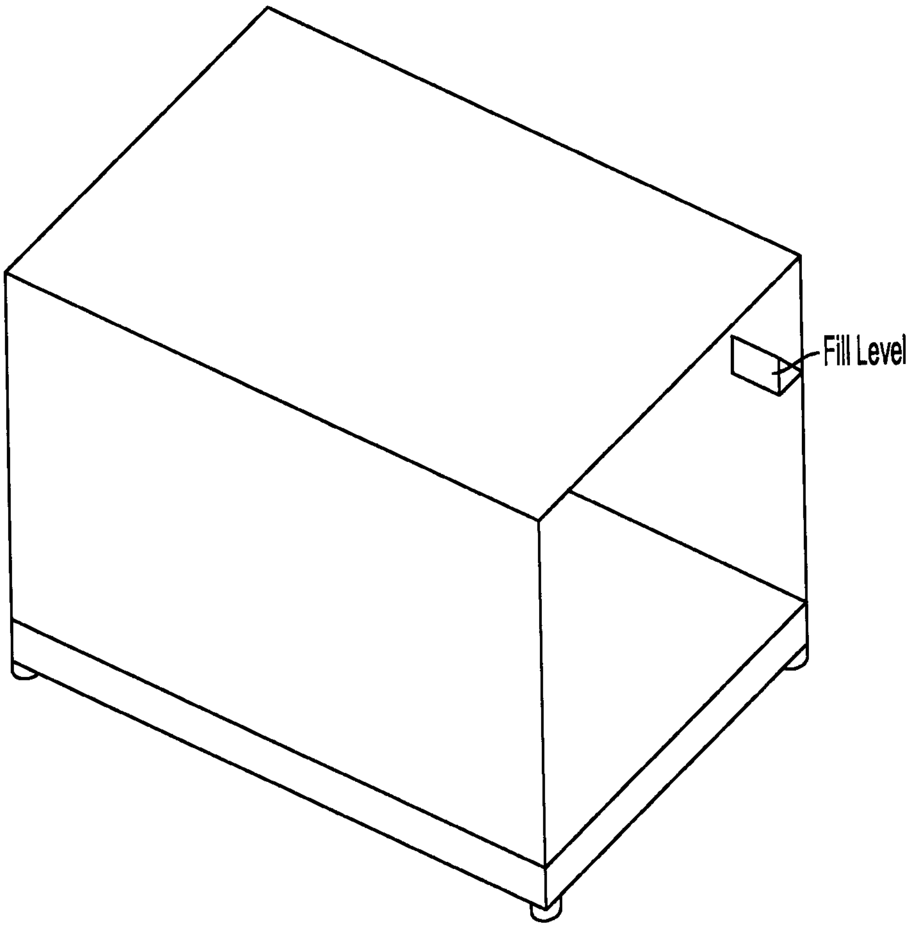
FIG. 2 is a perspective view of a smart bin according to a particular embodiment in which the smart bin includes a physical fill level indicator.
Figure 3:
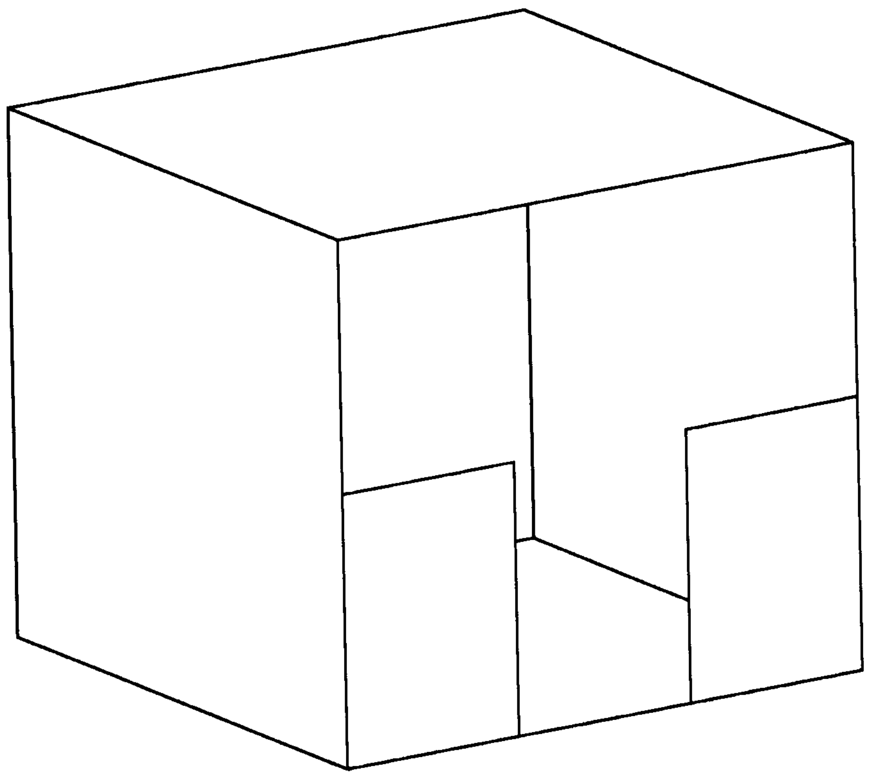
FIG. 3 is a perspective view of a cuboid-shaped smart bin having a substantially T-shaped opening in one side (e.g., a front side) through which a user may remove linens or other items.

As discussed above, in various embodiments, the linen management system comprises a network of smart bins that each include one or more integrated scales that are configured to monitor the weight of the contents of the smart bin. The structure and functionality of smart bins according to various embodiments is shown and described in Appendix A of corresponding U.S. Provisional Application 63/337,876 (the '876 provisional application), which, as noted above, is incorporated herein by reference in its entirety. As shown in FIG. 3, in various embodiments, in particular embodiments, each smart bin comprises a housing having: (1) a substantially rectangular (e.g., square) bottom platform; (2) a substantially planar, rectangular (e.g., square) back wall that extends upwardly from a rear side of the bottom platform; (3) two substantially planar, substantially rectangular (e.g., square) co-facing side walls that extend upwardly from respective sides of the bottom platform so that the back wall and side walls form a continuous, substantially U-shaped wall that extends upwardly from a portion of the perimeter of the bottom platform; and (4) a substantially planar top portion that extends between the respective tops of the side walls and that at least substantially extends from a rear of the smart bin to a front of the smart bin. As shown in FIG. 2 of Appendix A, in particular embodiments, the smart bin may include a substantially planar partial front wall that cooperates with the co-facing side walls and the top portion to form a substantially T-shaped opening through which a user may grasp one or more linen items (e.g., sheets, surgical scrubs, pillow cases, etc.) and remove them from the bin's interior. In FIG. 3, the front wall includes two substantially planar, substantially rectangular wall portions that are offset from each other as shown in FIG. 3. In particular embodiments, the user may grasp linen items through the bottom, vertical portion of the T-shaped opening and remove the linen items through the upper, horizontal portion of the T-shaped opening. In alternative embodiments, the opening in the front of the bin may be any other suitable shape, such as a V-shaped or vertical rectangular opening.

In a particular embodiment, at least one of the smart bins is substantially in the shape of a substantially hollow cuboid defining an interior portion (e.g., a substantially cuboid-shaped interior portion) for storing linen items and a T-shaped opening in one of its sides through which a user may remove one or more linen items from the interior portion.

In various embodiments, the smart bin may further include at least one load cell that is positioned and otherwise configured to measure a weight of the smart bin. In a particular embodiment, such as the embodiment shown in FIG. 4, the smart bin includes four load cells, each of which is disposed adjacent (e.g., at) a respective corner of the bottom platform. Each smart bin may further include an onboard computing system comprising at least one computer processor and computer memory that is operatively connected to the at least one computer processor. The computing system may further include one or more output devices, such as a display, and one or more input devices, such as one or more input keys (e.g., keys of a keyboard), sensors, and/or buttons. In various embodiments, the display may be a touch screen display that may serve as an input device (e.g., by receiving touch input on the display itself).

The computing system may further include one or more suitable communications interfaces (e.g., one or more wireless networking interfaces, such as one or more wireless networking chips) that are connected to facilitate wireless communications between the smart bin and one or more remote computing devices (e.g., directly and/or via a suitable computing network such as a Local Area Network (LAN) and/or a Wide Area Network (WAN), such as the Internet. This may, for example, allow the smart bin's onboard computing system to communicate with other smart bins, and/or a centralized computing system that may be used to track and manage the inventory within a plurality of smart bins and/or other bins within a network of smart bins and related devices. FIG. 2 shows an example linen inventory management system with arrows indicating example data flows among the system's various components.

In various embodiments, each load cell (and/or one or more other sensors) may be operatively connected to the smart bin's computing system so that each load cell provides input to the smart bin's onboard computing system. As discussed in more detail below, the smart bin's computing system may, in various embodiments, be configured to use the data from the load cells to determine the number of particular items within the smart bin. The smart bin's computing system may be configured to then transmit this calculated inventory data to a centralized inventory management computing system, such as the centralized inventory management computing system described above. Alternatively, or in addition, the smart bin's computing system may be adapted to send data directly from the load cells to the inventory management system, which may then use the load cell data to calculate the inventory within the smart bin.

Visual Loading Indicators

In various embodiments, one or more of the individual smart bins include one or more integrated visual indicators for assisting a user in quickly loading the smart bin to PAR.

This may, for example, include a digital display, such as the display of the smart bin discussed above, that communicates how many items need to be added to, or removed from, the smart bin to reach PAR. In particular embodiments, the system determines the value to display by first using the weight information from the smart bin's load cells plus the known single-unit weight of items stored within the smart bin to determine how many items are currently within the smart bin. The system may, for example, first subtract the known weight of the bin portion of the smart bin from the total weight detected by the load cells to determine the weight of a payload within the bin, and then divide the payload weight by the single-unit weight of the type of item stored within the smart bin to determine the number of items within the smart bin. The system may then determine how many items need to be added or subtracted to bring the number of items within the smart bin to PAR by, for example, subtracting the determined number of items from the value of par. For example, if par is 10 fitted sheets and the system determines that the smart bin currently contains 8 fitted sheets, the system may determine that 10−8=2 fitted sheets need to be added to the smart bin in order to bring the smart bin to PAR.

Figure 5:
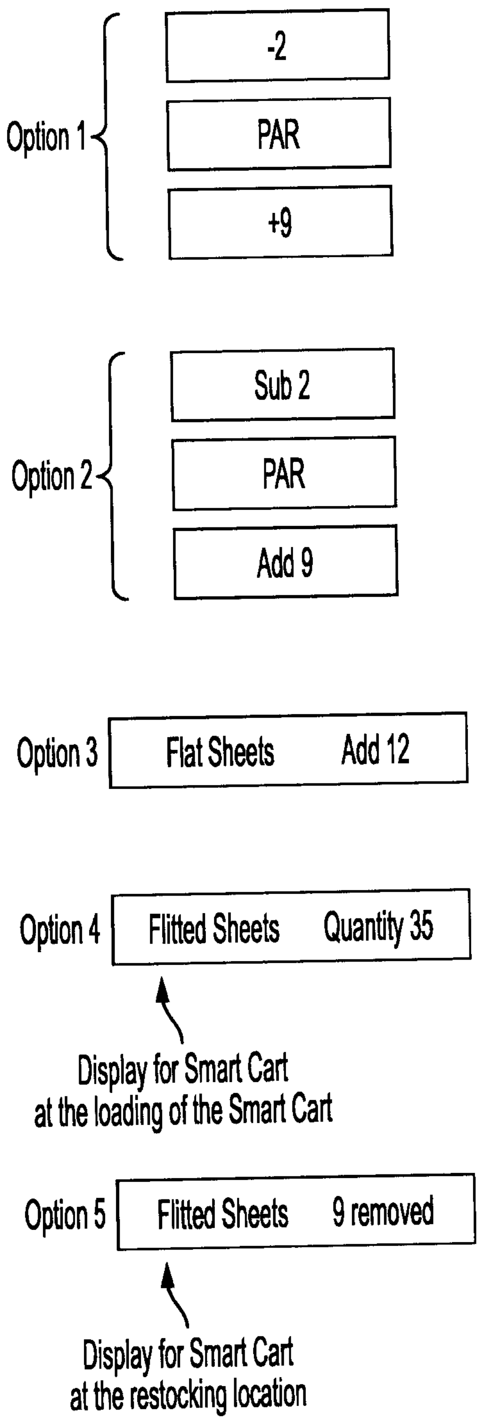
FIG. 5 includes graphical depictions of various user interface displays that would be suitable for use on various embodiments of the smart bin.

It should be understood that any suitable display format may be used to communicate to the user that they need to add or subtract items to bring the smart bin to PAR (or that the bin is currently at PAR). Various options are shown in FIG. 5.

One or more of the smart bins may also include a physical visual indicator (e.g., a mark and/or sticker) on the inside of the smart bin that indicates the height of a stack of a certain type of item when the smart bin is loaded to PAR. An example of such a physical indicator, in the form of a fill level sticker, is shown in FIG. 1 of Appendix A.

Use of Smart Bins within Secure Spaces, Smart Cabinets, and Smart Carts

Figure 1:
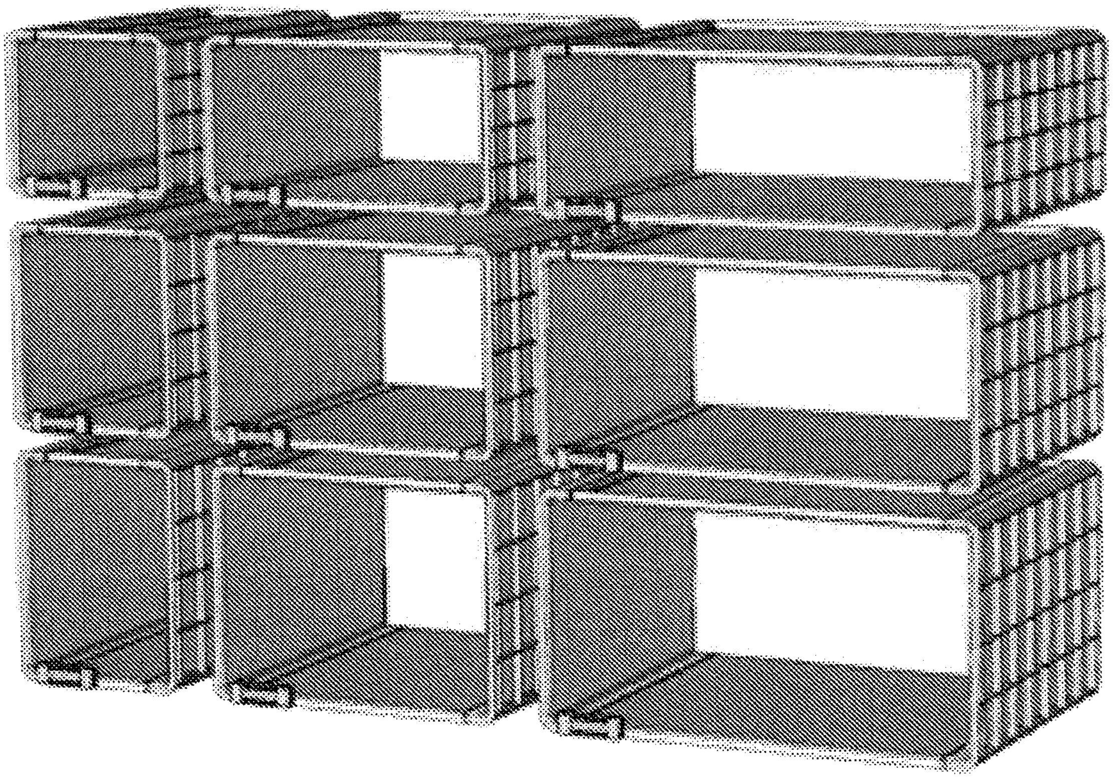
FIG. 1 is a perspective view of a 3×3 array of nine smart bins according to various embodiments.

In various embodiments, the smart bins are configured to be stackable, and to be deployed side-by-side as shown in FIG. 1. This figure shows nine smart bins that are arranged in a three-by-three array. In each column of smart bins, three bins are stacked on top of each other. The smart bins may be stacked in two-dimensional or three-dimensional arrays.

In such arrangements, in a particular implementation, each smart bin may be used to only store a particular type of item, such as a particular type of linen for any particular route. For example, for a particular route, the upper rightmost bin may be used to store fitted sheets and the upper leftmost bin may be used to store pillowcases.

Arrays of smart bins (or individual smart bins) may be deployed in any of a variety of different locations. For example, the smart bins may be deployed: (1) within an unsecure area; (2) within a secure area, such as a locked closet; (3) within a secure or unsecure cabinet; or (4) on a mobile cart, which is referred to below as a smart cart.

FIG. 2 shows an example configuration of a smart linen cabinet in which each square box shown within the interior of the cabinet represents a particular smart bin, such as the bins described above. This figure shows how the modular construction described in Appendix A may be useful in constructing an array of smart bins that fit within a particular size of cabinet. It should be understood that the smart bins may vary in width or height as needed, and that the smart bins may be stacked directly upon top of each other or that one or more of the horizontal rows of smart bins may be separated by shelves.

FIG. 2 also shows an example configuration of a smart cart where each square box represents a particular smart bin. In particular embodiments, the smart cart includes a housing (e.g., a substantially rectangular housing) that defines an interior portion, such as a substantially rectangular interior portion. In various embodiments, the width of the smart cart may be about the depth of each of the smart bins (where each of the smart bins has at least about the same depth as the others within the smart cart). As with the smart cabinets discussed above, it should be understood that the smart bins may vary in width or height as needed, and that the smart bins may be stacked directly upon top of each other or that one or more of the horizontal rows of smart bins may be separated by shelves.

In a particular embodiment, the smart cart defines a substantially planar rear wall that is adjacent to the respective rear portions of the smart bins when the bins are stored within the smart cart and that may, for example, block access to the rear portion of one or more (e.g., each of) the smart bins that are stored within the smart cart. In particular embodiments, the smart cart may include a selectively lockable front door that is adapted to be selectively opened and closed to selectively provide access to the smart cart's secure interior.

In a further embodiment, the smart cart may be dimensioned to hold a two-deep array of smart bins. In this embodiment, each side of the smart cart may include a selectively lockable door to selectively provide access to one of the arrays of smart bins.

In particular embodiments, the smart cart includes one or more wheels that are each disposed adjacent a bottom portion of the smart cart to facilitate rolling the cart over a support surface. In particular embodiments, the cart includes four wheels (e.g., swiveled and/or fixed wheels), each being disposed adjacent a respective bottom corner of the cart. The cart may further include one or more handles, which may, for example, be attached adjacent an upper corner of the cart and positioned to allow a user to push and steer the cart over a support surface. In particular embodiments, the handle is an elongated handle having a length that is about the same as the depth of the cart and the handle may be mounted so that it is substantially parallel to the upper right hand corner of the cart, extending from a front to a rear portion of the cart.

When the smart bins are deployed within the context of a cabinet, the cabinet and smart bins may be configured substantially as described above in regard to smart carts, except that the cabinet may be larger than a typical smart cart, include more smart bins, and may or may not include wheels for repositioning the cabinet. In particular embodiments, the cabinet may not include a handle as described above, but other embodiments may include a suitable handle for positioning and repositioning the cabinet.

In particular embodiments, the cart and/or cabinet may include an on-board computing system (e.g., a suitable computer processor that is operatively coupled to memory, suitable input/output devices, a display, and networking hardware). In particular embodiments, the on-board computing system is similar to the on-board computing system of the smart bins except that the display of the cart and/or cabinet may, for example, be larger than the individual displays of the smart bins. In various embodiments, the on-board computing system is a tablet that is mounted to a user-facing portion of the smart cart or smart cabinet and connected to a suitable power supply (e.g., a battery supply on the smart cart or a power supply on the cabinet).

In particular embodiments, the computing system of the smart cart may be configured to communicate directly or indirectly with the computing systems of the various respective smart bins within the smart cart so that the computing system of the smart cart can monitor the inventory of each of the smart bins on the smart cart at least substantially in real time (e.g., in real time). The computing system of the smart cart may further include software for displaying instructions and other information to an operator of the smart cart.

In particular embodiments, the smart cart's software comprises computer-executable instructions that are stored within a non-transitory computer-readable medium (e.g., computer memory) that is operatively associated with the smart cart's computer system. The computer-executable instructions may, for example, be configured to display instructions and other information to an operator of the cart to assist in efficiently loading the smart cart with an appropriate linens or other items. In particular embodiments, the smart cart's software may provide a centralized display of instructions that communicate to the user how many of a particular item needs to be loaded into each respective bin within the smart cart to bring the bin to PAR. In various embodiments, to facilitate compliance with these instructions, the system may provide instructions on both a centralized display associated with the smart cart and on respective individual displays associated with each of the smart cart's various smart bins.

For example, the smart cart's central display may instruct a user to load 10 baby blankets into a "baby blanket" smart bin on the smart cart. When these instructions are these displayed, the system may display the text "Baby Blankets" on a particular smart bin that has been designated to store baby blankets. Accordingly, after reading the instructions to load 10 baby blankets on the smart cart's central display, the operator would then locate the smart bin labeled "Baby Blankets" and then load 10 baby blankets into that smart bin.

In further embodiments, the smart cart's computing system may use a similar process to provide instructions for unloading each smart bin to properly stock a dispensing cabinet or other dispensing structure. For example, the smart cart's computing system may display instructions to unload a particular number of linens or other items from a particular smart bin on the smart cart (e.g., a smart bin labeled "Fitted Sheets") to a particular smart bin (also labeled "Fitted Sheets") on a stationary cart that is located within a secure area on a particular floor of a hospital. The smart bin's computer system may include this type of information for loading each smart bin within the stationary cabinet with inventory from corresponding smart bins on the smart cart.

In particular embodiments, the smart cart's computing system may display instructions for loading and/or unloading the dispensing cabinet's smart bins sequentially (e.g., one at a time), or simultaneously. In some embodiments, the smart cart's computing system may include an indication of the amount of time that the operator should spend in loading the linens or other items from a particular smart bin on the smart cart into a corresponding smart bin in the dispensing cabinet. For example, the system may display an indication that the user should take 15 seconds or less to complete this process. In various embodiments, the system may display a timer that provides a countdown of a target time for completing this process. For example, the system may display a 15-second timer for loading the linens or other items from a particular smart bin on the smart cart into a corresponding smart bin on the dispensing cabinet.

The smart cart's computing system may further include navigation information that is useful in helping a smart cart operator identify and find a next target location (e.g., on a particular linen stocking route within a hospital). In a particular embodiment, the smart cart may include suitable GPS hardware to track the smart cart's current location. Additionally, or alternatively, the smart cart's computing system, or a related inventory management computing system, may include additional functionality for tracking the current location of the smart cart. For example, an inventory management system may use information regarding which router(s) or wireless beacon(s) the smart cart's wireless card is communicating with (optionally along with other information) to determine a particular current location of the smart cart. The smart cart's computing system or inventory management system may then use suitable navigation software to, for example, communicate navigation instructions to a user on the smart cart's display to help the user navigate from their current location to their next stocking location. Such navigation instructions may include, for example, a map from the operator's current location to their next stocking location, or verbal and/or written word instructions telling the operator how to move from their current location to their next stocking location.

In particular embodiments, the smart cart's computing system and/or inventory management system may gamify the navigation process by, for example, displaying a target time for traveling each respective leg of the stocking route (e.g., the user should take 5 minutes—or other pre-determined amount of time—or less to travel from a cabinet in a first location within the hospital to a cabinet in a second location within the hospital). In various embodiments, the smart cart's display would display an indication of the target time, optionally along with an indication of the operator's progress in meeting the target. In various embodiments, the system may assign the user a score that is displayed (e.g., in real time as the user works) to provide feedback to the user regarding their performance as they do their job.

Inventory Management System

In various embodiments, the system may include a centralized inventory management system that may, for example, help hospital administrators or other individuals track the usage of linen and/or other items, and related stocking levels. In particular embodiments the system may be adapted to update this information substantially in real time by receiving information at least substantially in real time from all of (or any particular subset of) the various smart bins, smart carts, and/or smart cabinets within a particular facility in real time. This may be done, for example, by having the various smart bins, smart carts, and/or smart cabinets transmit this information at least substantially in real time (e.g., in real time) to one or more central servers associated with the inventory management system via one or more suitable networks, such as one or more Local Area Networks (LANs) and/or one or more Wide Area Networks (WANs), such as the Internet. FIG. 2 shows an example network configuration according to various embodiments, where the "computer" may represent one or more suitable computers, such as a central inventory management server (e.g., a linen management server) that may either be in the same location as the smart carts/smart cabinets or remote from that location. In this figure, the arrows represent potential data flows between the various system components.

Figure 4:
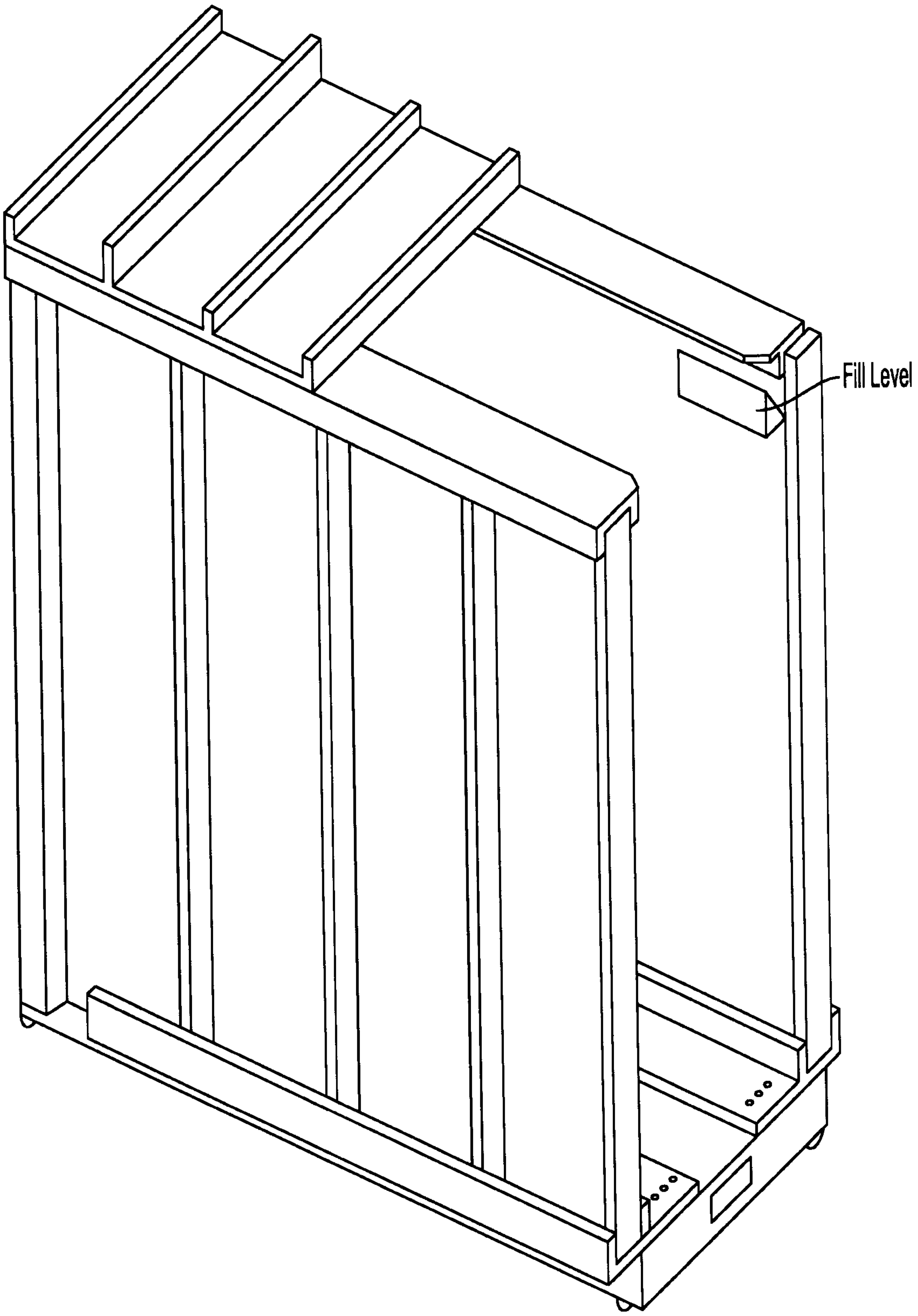
FIG. 4 is a perspective view of a cuboid-shaped smart bin having an open front portion.

In particular embodiments, the inventory management system may be adapted to display appropriate linen inventory information (e.g., from the various smart bins, smart carts, and/or smart cabinets) and/or data reflecting this information on any suitable computing device, such as a laptop computer, or handheld computing device, such as a smart phone. The inventory management system may further be adapted to display smart cart operator information on this same interface and/or on another interface. Accordingly, in various embodiments, the inventory management system may be adapted to determine and/or display: (1) current inventory levels of the various smart bins, smart carts, and/or smart cabinets within a particular facility or multiple facilities; (2) operator performance data (e.g., the average time that it takes each operator to complete a particular stocking route and/or particular legs of the route); and/or (3) other related information, such as linen usage rates, linen loss rates, etc. FIGS. 3-5 show various example displays of such data.

Example Operation of Smart Cart

In various embodiments, the smart cart and system are configured so that, when the system detects that the smart cart is adjacent and/or in a linen room (that contains linen used to restock smart carts), the smart cart and/or other suitable component of the linen inventory management system automatically determines that the smart cart has completed its current route. The system may then determine a next route that the smart cart is to be used for (e.g., by referencing an electronic schedule that is stored in system memory), or alternatively, a user may manually input an indication of a next route into the system (e.g., via a suitable user interface on the smart cart). The system may then at least substantially automatically determine what inventory the smart cart may need for the determined/input next route (e.g., how many of each particular item will be needed to complete the new route).

In particular embodiments, the system and/or smart cart may then automatically facilitate reconfiguring the smart cart for the next route. For example, the smart cart may: (1) determine which of the smart bins on the smart cart need to carry a different type of item for the new route; (2) for each smart bin that needs to carry a different type of item, change the display on the smart bin so that instead of displaying the name of the item that is currently stored in the smart bin, the smart bin displays: (a) the name of the new type of item that is to be stored in the smart bin for the new route, and (b) optionally a number of items that is to be loaded into the bin; and (3) for each smart bin that needs to carry a different type of item, initiate an alert sequence for the smart bin—initiating this alert sequence may, for example, include causing the smart bin's display to flash and/or causing an audio output device associated with the smart bin to generate an auditory alert—the purpose of the alert sequence is to bring the operator's attention to the smart bin.

In various embodiments, the system and/or smart bin are configured to determine a unit weight of the new type of item that is to be stored within each of the identified smart bins for the new route. The system may determine this unit weight, for example, by retrieving this information from an operator (e.g., by prompting the operator to enter this information via a suitable user interface), or from a suitable data structure, such as a database that includes information on the various items that will be needed for the new route and the respective unit weights of each of the items. The system may use the unit weight information, as discussed above, to determine a current number of items that are within the respective smart bins (e.g., by dividing a total weight of items that are stored within the bin by the unit weight).

The system may be further configured to determine when an operator has replaced a particular identified smart bin's current inventory with the new items. The system may begin this process, for example, by monitoring a weight of items within the smart bin (e.g., continuously and/or on a periodic basis) and, in response to determining that the weight of items stored within the bin has gone from a positive value to zero or about zero, the system may determine that the user has removed all of the previous items from the smart bin. The system may then continue monitoring the weight of items that are stored within the smart bin. In response to determining that the weight of items stored within the smart bin is no longer zero or about zero, the system may divide the weight of items stored within the smart bin by the unit weight of the items that the system has determined should be stored within the smart bin. If the result of this division is at least about a particular whole number (e.g., 7, 7.005, 6.003, etc.), the system will determine that the smart bin has been at least partially loaded with the correct new items. If not, the system may display a suitable alert to the operator, for example, telling the operator to confirm that the correct type of item has been loaded into the smart bin.

If the result of the above-referenced division is a whole number, the system may use this number to determine whether the number of new items within the smart bin is the correct number of items needed for the new route (e.g., by determining whether the number matches the number of items needed for the route). If the number of items is not the correct number needed for the route, the system may communicate instructions to the user for adding or removing items until the smart bin is loaded to the proper level. This may be done, for example, by displaying suitable instructions on the smart bin's display.

In particular embodiments, in response to the system determining that a user has removed all items from a particular smart bin and started to load new items into the particular smart bin (e.g., using the technique described above or any other suitable technique), the system may automatically stop the smart bin from displaying a "changeover needed" alert to a user (e.g., the system may stop one or more lights and/or displays associated with the smart bin from flashing and/or change the rate at which the one or more lights and/or displays flashes, change the color of the smart bin from a first color to a second color or no color, etc.). This may serve as an indication that the smart cart no longer needs a changeover in the type of items that it currently holds.

Similarly, in particular embodiments, in response to the system determining that at least a pre-determined "correct" number of new items has been loaded into a particular smart bin as part of a changeover (and/or that more than the correct items have been loaded into the particular smart bin), the system may automatically stop the smart bin from displaying a "modify number of items" alert to a user (e.g., the system may stop one or more lights and/or displays associated with the smart bin from flashing and/or change the rate at which the one or more lights and/or displays flashes, change the color of the smart bin from a first color to a second color or no color, etc.). This may serve as an indication that the smart cart has been successfully loaded with at least the proper number of items needed for the new route.

As a particular example, in response to determining that a particular smart bin requires a changeover in items, the system may cause the smart bin's display to flash at a first rate. In response to determining that the user has removed all items from the smart bin, the system may determine that a changeover of items no longer needs to be completed and cause the smart bin's display to flash at a second rate (e.g., which may be slower than the first rate) until it determines that the particular smart bin has been loaded with a number of items that is greater than or equal to a pre-determined "correct" number of items that is to be loaded into the particular smart bin. In response to making this determination, the system may then stop the smart bin's display from flashing. This may, for example, indicate that the smart bin contains enough items for the next route.

As an alternative to the above process, rather than automatically determining whether a user has replaced a particular identified smart bin's current inventory with the new items, the system may be configured to receive input from a user (e.g., via a suitable user interface) indicating that the user has replaced a particular identified smart bin's current inventory with the new items (e.g., a sufficient number of new items for the new route).

As noted above, the system may facilitate having the user load each of the smart bins until each of the smart bins contains the amount of the respective item to be stored within the smart bin needed to complete the new route. For example, as indicated above, for each respective smart bin, the system may display a number on the smart bin's display that indicates an amount of items that needs to be loaded into, or removed from, the smart bin in order to adjust the number of items so that the number of items in the respective smart bin is the number needed for the current route. For example, the system may display "Baby Blankets +4" on a smart bin that needs to have four more baby blankets added to it in order to have the appropriate number of baby blankets to complete the new route. Similarly, the system may display "Baby Blankets −3" if three baby blankets need to be removed from the smart bin in order to have the appropriate number of baby blankets to complete the new route.

In various embodiments, the system may determine how many of each particular type of item is needed to complete the new route in any suitable way. In a particular embodiment, the system may use various types of information to make this determination (where the information may be maintained in any suitable computing device, such as one or more central servers associated with the system). Such information may include, for example: (1) inventory information (e.g., current inventory information) received from the various smart bins along the route (e.g., inventory information from each bin on the route); (2) for one or more smart bins on the new route (e.g., all smart bins on the new route), historical inventory information indicating the rate of inventory changes over time for each smart bin; (3) for each other type of distribution location on the route (e.g., each non-computerized distribution bin and/or location—such as closets/shelves) historical inventory information indicating the rate of inventory changes over time for each of the distribution locations. The historical inventory information referenced above may be, for example, specific to one or more of: (1) the time of day that the new route is to be serviced; (2) the day of week that the new route is to be serviced; (3) the time of year that the new route is to be serviced; and/or (4) the current occupancy rate of one or more portions of the hospital that are to be serviced by the route.

For example, in a particular embodiment, the system may determine the number of a particular item that is to be loaded onto the smart cart by adding the following values together: (1) the number of items needed to bring each smart bin on the route that contains the particular item to PAR, based, for example, on current and/or recent inventory data for each smart bin on the route; (2) for each particular smart bin on the route containing the item, the number of the particular item that is forecast (e.g., based on the historical information noted above) to be removed from the smart bin by the time the smart cart arrives at that particular smart bin (this calculation may be based, for example, on the number of the particular type of item that would typically be removed from the particular smart bin from the current time until a time that the smart cart is forecast to arrive at the particular smart bin); (3) the number of items that the system forecasts will be needed to fill each other type of distribution location on the route (e.g., each non-computerized distribution bin and/or location), which, as noted above, may be based, for example, on: (1) the last known inventory level of each of the other distribution locations and (2) historical inventory information indicating the rate of inventory changes over time for each of the distribution locations.

In various embodiments, the system may determine, at an appropriate time, whether one or more of the smart cart's smart bins includes the specified number of items. For example, the system may determine that the user has begun loading items into the smart bin but has not loaded any more items for a predetermined period of time, or that smart cart has begun servicing the route (e.g., has left the linen room), but that the specified number of items is not loaded into a particular smart bin on the smart cart. In response to determining that one or more of the smart cart's smart bins don't include the specified number of items, the smart cart may display a message to the user indicating that the correct number of items hasn't been loaded into the smart bin. In addition, the smart cart may display a message to a user prompting the user to indicate why they didn't fill the one or more smart bins to the level indicated by the smart cart and/or smart bin. For example, the system may request that the user indicate whether: (1) no additional items of the correct type were available to add to the smart bin; (2) insufficient space was available within the smart cart's various smart bins (or elsewhere on the smart cart); or (3) the operator made a mistake or wasn't motivated to fill the smart bin properly.

In various embodiments, if the operator selects option 1, this may indicate that a laundry service associated with the hospital (or other healthcare facility) is not delivering enough laundry of a particular type to the linen room to meet the needs of the hospital. To determine whether this is the case, the system may access information from a hospital occupancy database or other suitable data structure indicating the hospital's current occupancy level and/or other related information. The system may then use this information to determine whether the current shortage of the particular type of linen is based on an unusually high occupancy level within the hospital, or some other factor (e.g., not enough laundry of that particular type being delivered to the linen room by the laundry service).

As a specific example, in a particular embodiment, if the operator selects option 1, a central computer may determine whether insufficient inventory of a particular type is being delivered from a laundry service by analyzing data for a pre-determined number of days, and then using a suitable algorithm that may include, for example, historical linen usage information for the route at issue and information regarding hospital occupancy levels that would impact the route at issue (e.g., hospital and department patient days). If the patient days are normal or low, the system may determine that the inventory level needs to be increased to satisfy demand. In response to making this determination, the system may generate an appropriate alert indicating that inventory of one or more particular items of linen need to be increased. This message may be transmitted to a suitable individual (e.g., via a suitable electronic message) who may then coordinate any suitable inventory changes.

In a particular embodiment, if the system determines that not enough laundry of a particular type is being delivered to the linen room, the system may automatically generate an automatic alert to one or more particular individuals to alert them of this issue and/or to coordinate one or more future deliveries of the particular type of linen at issue. For example, the system may generate an automated message (e.g., an auto-generated email) that includes text indicating that there is a shortage of baby blankets, or other items, in the hospital's linen room. The system may then send this message to a linen room supervisor who may then use that information, for example, to adjust inventory levels of baby blankets within the linen room. As a further example, the system may place an automatically generated order for additional baby blankets (or other items) substantially without involvement from a human user. In a particular embodiment, the system may optionally schedule a supplemental delivery (e.g., via another smart cart) to one or more locations on the route at a current or future time to assure that the route is properly restocked.

Returning to the discussion above, if the user selects option 2 (e.g., that insufficient space was available within the smart cart's various smart bins (or elsewhere on the smart cart), the system may, in response, generate and communicate a suitable alert to a user indicating that the smart cart may need to be reconfigured for the current or future routes to assure that the cart includes suitable space for the inventory needed to supply the route.

In particular embodiments, if the user selects option 3 (e.g., that the operator made a mistake or wasn't motivated to fill the smart bin properly), the system may automatically generate and transmit an appropriate message to the operator's supervisor and/or other suitable individual, who may use that information in coordinating appropriate training and/or making compensation decisions.

Alternative Methods of Determining Inventory Levels

While various embodiments may involve determining a number of a particular type of item that is stored within a particular bin (e.g., smart bin) or other receptacle or storage space based on the weight of the items, it should be understood that other methods may be used to make this determination. For example, in various embodiments, each smart bin may include one or more digital cameras that are positioned to capture one or more images of the contents of the bin and to communicate the captured one or more images to one or more computer processors associated with the system (e.g., one or more computer processors associated with the smart bin and/or one or more remote computer processors). These one or more images may then be processed to determine a number of a particular type of item in the bin. For example, the interior of the bin may include one or more inventory markers (e.g., one or more substantially horizontal marks—e.g., numbered marks—on one or more interior walls of the bin) that each indicate a respective fill level of the bin. In various embodiments, the system may include software that is configured to determine the current inventory of the smart bin based on which inventory markers are visible (and which are obstructed) in the one or more images. For example, if a bin containing flat sheets is filled up to a fill level mark labeled "9" (e.g., fill level marks 1-8 are all obstructed with flat sheets), the system may determine that the bin contains nine flat sheets. As an alternative example, various images of different inventory levels may be used to train a suitable machine learning algorithm to automatically determine a current inventory level of one or more smart bins based on images of the smart bin's current inventory.

It should be understood that the one or more cameras referenced above may be integrated into a particular smart bin (or other receptacle or storage space) or be located remote from the particular smart bin (or other receptacle or storage space). In various embodiments, at least two cameras are disposed adjacent an upper portion of each smart bin and directed to capture images of the contents of the smart bin. This may allow the system to continue capturing data if one of the cameras becomes obstructed.

In alternative embodiments, any other suitable mechanism may be used for determining the amount of inventory within each smart bin. For example, in alternative embodiments, a system may use light and/or sound based item-tracking techniques (e.g., auditory item tracking techniques) to track the inventory of items within the bin. In further embodiments, one or more (e.g., each) of the linen items within a particular bin may include an integrated RFID tag and the system may include one or more RFID readers (e.g., integrated into each smart bin) that the system uses to track the inventory of the items within one or more of the respective smart bins by reading the respective RFID tags and thereby knowing which items are present within each bin.

Example Technical Platforms

As will be appreciated by one skilled in the relevant field, systems and methods for managing linen inventory, according to various embodiments described herein, may be, for example, embodied as a computer system, a method, or a computer program product. Accordingly, various embodiments may take the form of an entirely hardware embodiment, an entirely software embodiment, or an embodiment combining software and hardware aspects. Furthermore, particular embodiments may take the form of a computer program product stored on a computer-readable storage medium having computer-readable instructions (e.g., software) embodied in the storage medium. Various embodiments may take the form of web, mobile, and/or wearable computer-implemented computer software. Any suitable computer-readable storage medium may be utilized including, for example, hard disks, compact disks, DVDs, optical storage devices, and/or magnetic storage devices.

It should be understood that each step described herein as being executed by a linen inventory management system or systems (and/or other steps described herein), and any combinations of such steps, may be implemented by a computer executing computer program instructions. These computer program instructions may be loaded onto a general purpose computer, special purpose computer, or other programmable data processing apparatus to produce a machine, such that the instructions which execute on the computer or other programmable data processing apparatus to create means for implementing the various steps described herein.

These computer program instructions may also be stored in a computer-readable memory that may direct a computer or other programmable data processing apparatus to function in a particular manner such that the instructions stored in the computer-readable memory produce an article of manufacture that is configured for implementing the function specified in the flowchart step or steps. The computer program instructions may also be loaded onto a computer or other programmable data processing apparatus to cause a series of operational steps to be performed on the computer or other programmable apparatus to produce a computer implemented process such that the instructions that execute on the computer or other programmable apparatus provide steps for implementing the functions specified in the flowchart step or steps.

Accordingly, the descriptions, above, of various computer-implemented steps support combinations of mechanisms for performing the specified functions, combinations of steps for performing the specified functions, and program instructions for performing the specified functions. It should also be understood that each step, and combinations of such steps, may be implemented by special-purpose hardware-based computer systems that perform the specified functions or steps, or combinations of special purpose hardware and other hardware executing appropriate computer instructions.

Example System Architecture

Figure 6:
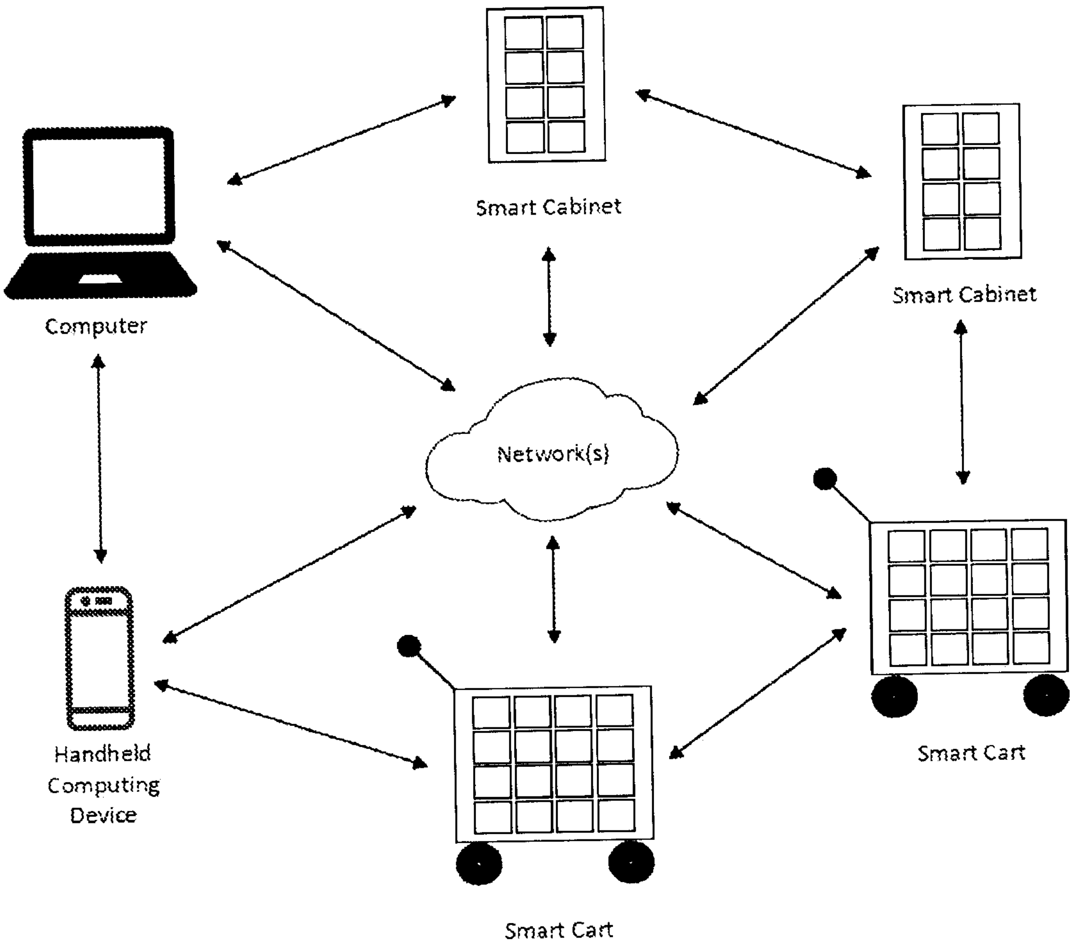
FIG. 6 is a diagram showing how multiple smart carts, smart cabinets, and computing devices may be communicatively linked via a network.

FIG. 6 is a block diagram of a system 100 according to a particular embodiment. As may be understood from this figure, the system 100 may include one or more computer networks 110, a server 120, a storage device 130 (that may, in various embodiments, contain one or more databases of information that may include personal data), and/or one or more client computing devices such as a tablet computer 140, a desktop or laptop computer 150, a handheld computing device 160 (e.g., a cellular phone, a smart phone, etc.), a browser and Internet capable set-top box 170 connected with a television (e.g., a television 180), and/or a smart television 180 having browser and Internet capability. The client computing devices attached to the network may also, or instead, include scanners/copiers/printers/fax machines 190 having one or more hard drives. The server 120, client computing devices, and storage device 130 may be physically located in a central location, such as the headquarters of an organization, for example, or in separate facilities. The devices may be owned or maintained by employees, contractors, or other third parties (e.g., a cloud service provider, a copier vendor). In particular embodiments, the computer networks 110 facilitate communication between the server 120, one or more client computing devices 140, 150, 160, 170, 180, 190, and storage device 130.

The computer networks 110 may include any of a variety of types of wired and/or wireless computer networks and any combination therefore, such as the Internet, a private intranet, a public switched telephone network (PSTN), or any other type of network. The communication link between the server 120, one or more client computing devices 140, 150, 160, 170, 180, 190, and storage device 130 may be, for example, implemented via a Local Area Network (LAN), a Wide Area Network (WAN), and/or via the Internet.

Example Computer Architecture

Figure 7:
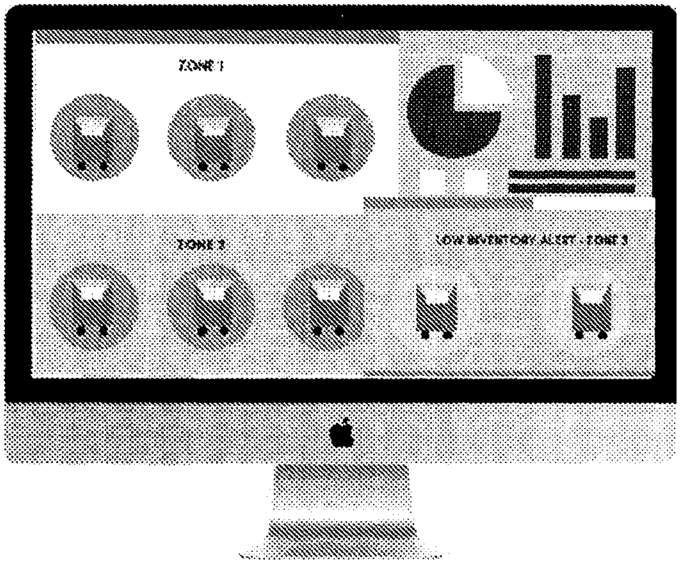
FIGS. 7-9 are examples of suitable user interfaces according to various embodiments.
Figure 8:
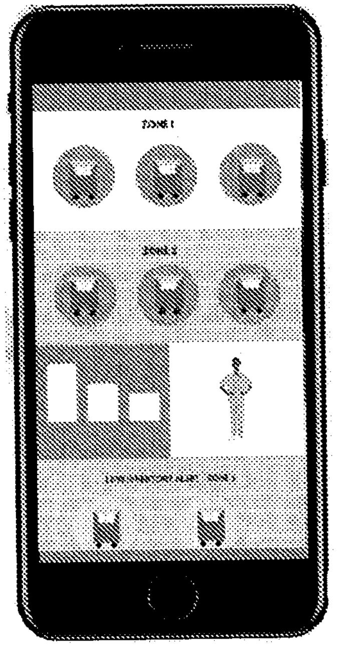
Figure 9:
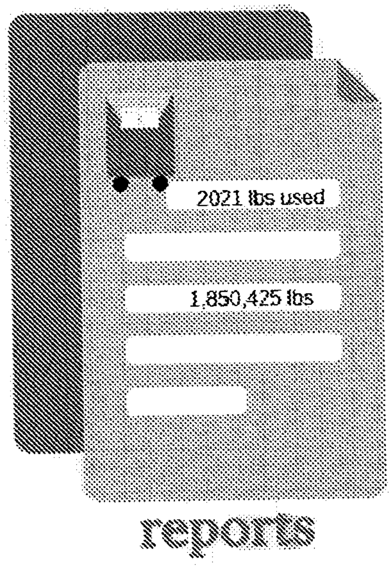
Figure 10:
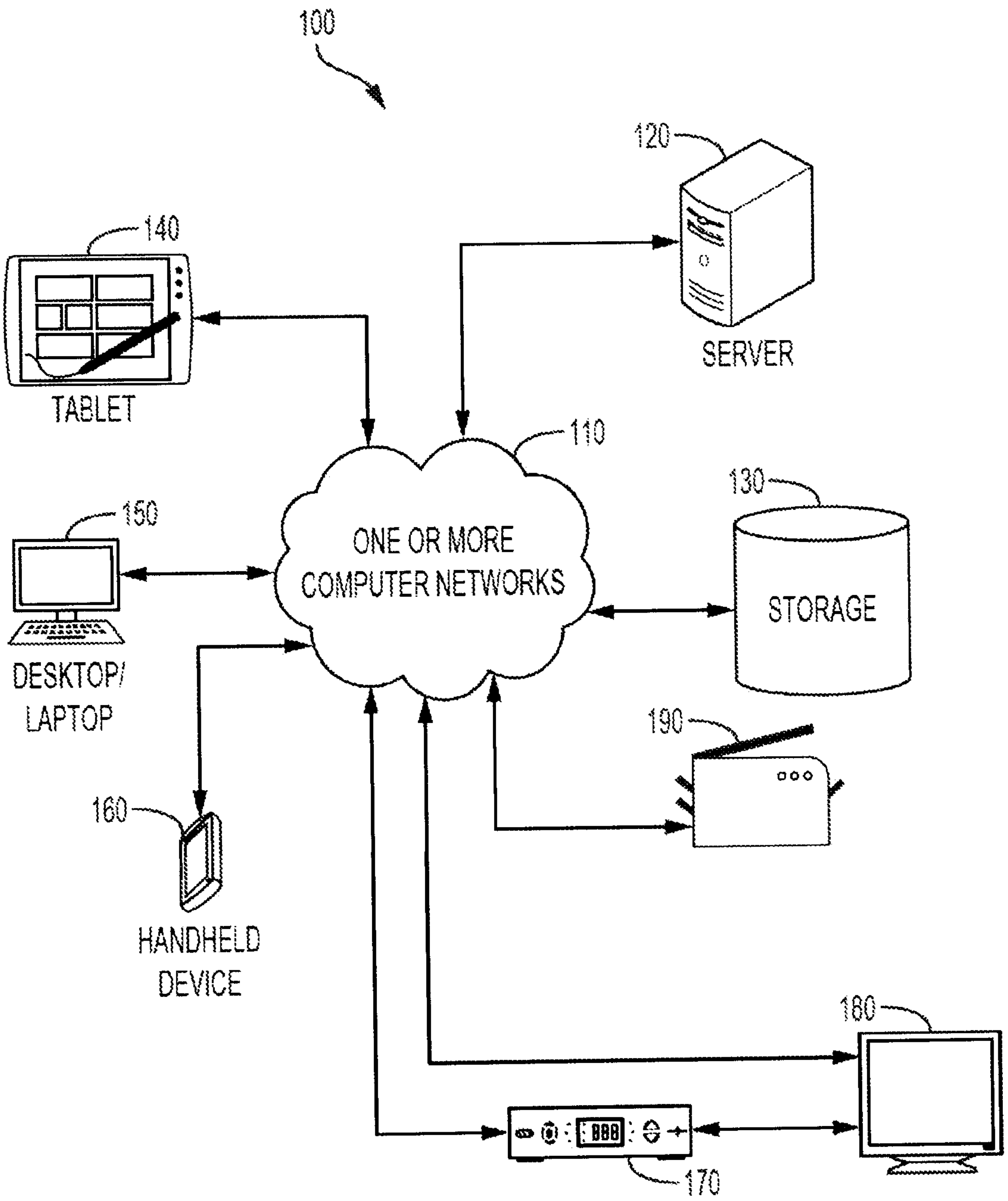
FIG. 10 is an example network environment in which the present system and methods may operate.
Figure 11:
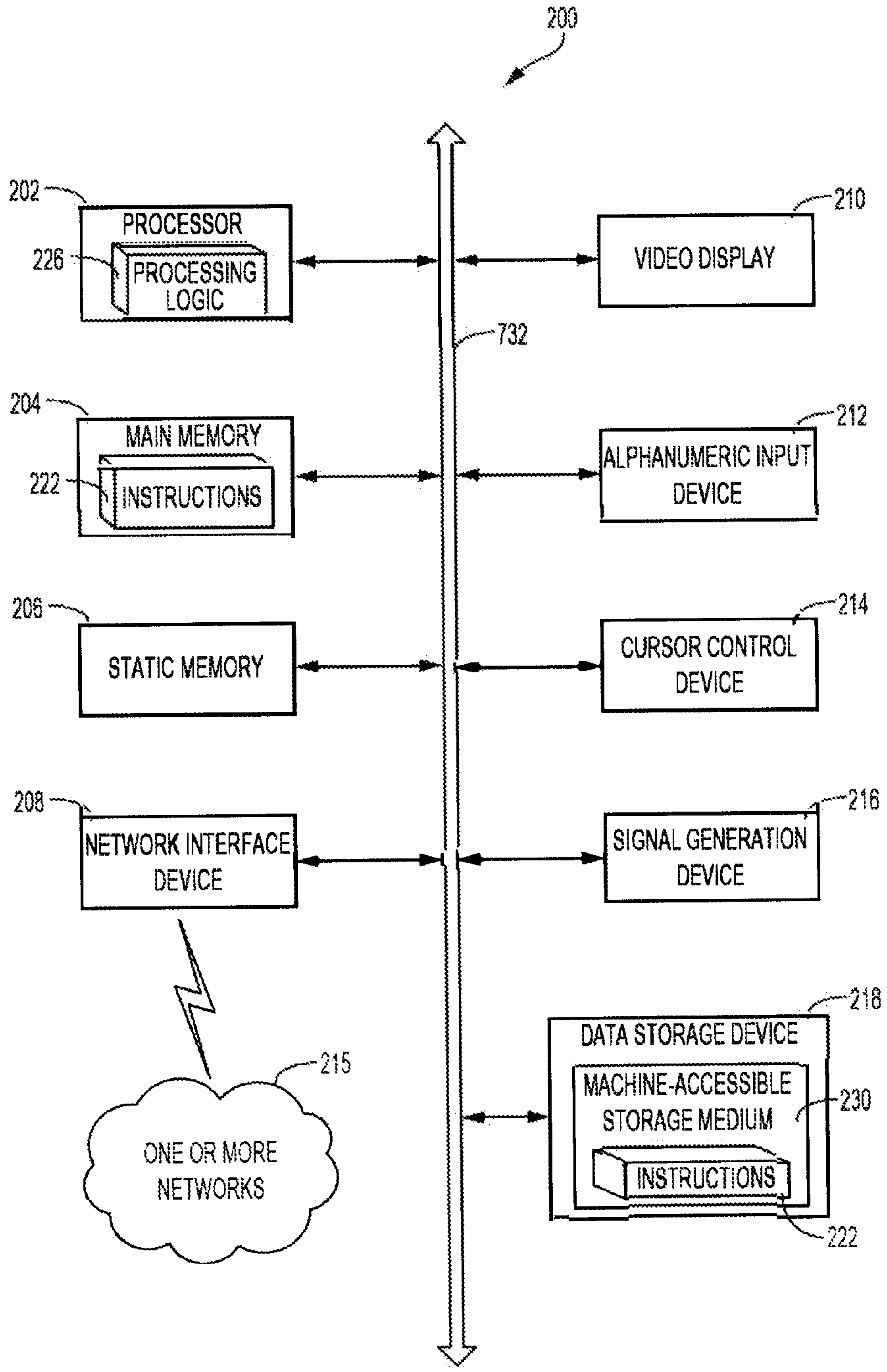
FIG. 11 is a schematic diagram of a computer that is suitable for use in various embodiments.

FIG. 7 illustrates a diagrammatic representation of the architecture of a computer 200 that may be used within the system 200, for example, as a client computer (e.g., one of computing devices 140, 150, 160, 170, 180, 190, shown in FIG. 6) and/or as a server computer (e.g., server 120 shown in FIG. 6). In exemplary embodiments, the computer 200 may be suitable for use as a computer within the context of the system 600 that is configured to operationalize the various aspects of the exemplary unstructured data redaction systems describe herein. In particular embodiments, the computer 200 may be connected (e.g., networked) to other computers in a LAN, an intranet, an extranet, and/or the Internet. As noted above, the computer 200 may operate in the capacity of a server or a client computer in a client-server network environment or as a peer computer in a peer-to-peer (or distributed) network environment. The computer 200 may be a personal computer (PC), a tablet PC, a set-top box (STB), a Personal Digital Assistant (PDA), a cellular telephone, smart phone, a web appliance, a server, a network router, a switch or bridge, or any other computer capable of executing a set of instructions (sequential or otherwise) that specify actions to be taken by that computer. Further, while only a single computer is illustrated, the term "computer" as used herein shall also be taken to include any collection of computers that individually or jointly execute a set (or multiple sets) of instructions to perform any of the methodologies discussed herein.

The exemplary computer 200 may include a processor 202, a main memory 204 (e.g., read-only memory (ROM), flash memory, dynamic random access memory (DRAM) such as synchronous DRAM (SDRAM) or Rambus DRAM (RDRAM), etc.), a static memory 206 (e.g., flash memory, static random access memory (SRAM), etc.), and/or a data storage device 218, which communicate with each other via a bus 232.

The processor 202 represents one or more general-purpose processing devices such as a microprocessor, a central processing unit, or the like. More particularly, the processor 202 may be a complex instruction set computing (CISC) microprocessor, a reduced instruction set computing (RISC) microprocessor, a very long instruction word (VLIW) microprocessor, or a processor or processors implementing other instruction sets and/or any combination of instruction sets. The processor 202 may also be one or more special-purpose processing devices such as an application specific integrated circuit (ASIC), a field programmable gate array (FPGA), a digital signal processor (DSP), network processor, or the like. The processor 202 may be configured to execute processing logic 226 for performing various operations and steps discussed herein.

The computer 200 may further include a network interface device 208. The computer 200 also may include a video display unit 210 (e.g., a liquid crystal display (LCD) or a cathode ray tube (CRT)), an alphanumeric input device 212 (e.g., a keyboard), a cursor control device 214 (e.g., a mouse), and/or a signal generation device 216 (e.g., a speaker). The data storage device 218 may include a non-transitory computer-readable storage medium 230 (also known as a non-transitory computer-readable storage medium or a non-transitory computer-readable medium) on which may be stored one or more sets of instructions 222 (e.g., software, software modules) embodying any one or more of the methodologies and/or functions described herein. The software 222 may also reside, completely or at least partially, within the main memory 204 and/or within the processor 202 during execution thereof by computer 200, the main memory 204 and the processor 202 also constituting computer-accessible storage media. The software 222 may further be transmitted or received over a network 220 via network interface device 208.

While the computer-readable storage medium 230 is shown in an exemplary embodiment to be a single medium, the terms "computer-readable storage medium" and "machine-accessible storage medium" should be understood to include a single medium or multiple media (e.g., a centralized or distributed database, and/or associated caches and servers) that store the sets of instructions. The term "computer-readable storage medium" should also be understood to include any medium or media that is capable of storing, encoding, and/or carrying a set of instructions for execution by a computer and that cause a computer to perform any one or more of the methodologies of described herein. The term "computer-readable storage medium" should accordingly be understood to include, but not be limited to, solid-state memories, optical and magnetic media, etc.

Exemplary System Platform

According to various embodiments, the processes and logic flows described in this specification may be performed by a system (e.g., system 100) that includes, but is not limited to, one or more programmable processors (e.g., processor 202) executing one or more computer program modules to perform functions by operating on input data and generating output, thereby tying the process to a particular machine (e.g., a machine programmed to perform the processes described herein). This includes processors located in one or more of client computers (e.g., client computers 140, 150, 160, 170, 180, 190 of FIG. 6). These devices connected to the computer networks 110 may access and execute one or more Internet browser-based program modules that are "served up" through the computer networks 110 by one or more servers (e.g., server 120 of FIG. 6), and the data associated with the program may be stored on a one or more storage devices, which may reside within a server or computing device (e.g., main memory 204, static memory 206), be attached as a peripheral storage device to the servers or computing devices, and/or attached to the network (e.g., storage 130).

Advanced Processing in Various Embodiments

In various embodiments, the linen inventory management system uses advanced processing techniques to forecast linen usage, determine the number of one or more items needed for a particular route, etc. In particular embodiments, the linen inventory management system may forecast linen usage or determine the number of one or more items needed for a particular route using advanced processing techniques that may include artificial intelligence, machine learning, neural networking, big data methods, natural language processing, contextual awareness, and/or continual learning (in any combination). In various embodiments, the linen inventory management system may use any such advanced processing techniques to mine various data sources for linen usage information, hospital available bed count, or other information (such as other types of information noted above) that is stored therein to determine data types and relationships. In various embodiments, the linen inventory management system may use any such advanced processing techniques to perform any of the processing described herein to locate, identify, retrieve, modify, and/or perform any other functions related to determining current or future linen inventory levels, numbers of items needed to satisfy one or more linen restocking routes, etc.

Similar techniques (e.g., the use of AI, etc.) may be used by the system to determine inventory levels within a particular smart bin. For example, artificial intelligence software may be trained on a database of images (e.g., a large number of, for example about 50, about 100, about 1000 or more images) of one or more smart bins (e.g., taken at different times) that respectively include different known numbers of a particular linen item. The artificial intelligence software, based on its training, may then use this information to learn to determine the amount (e.g., number of) of linen items in a particular smart bin by analyzing one or more current images of the bin and/or the bin's contents.

In particular embodiments, one or more neural networks may be used to implement any of the advanced processing techniques described herein. A neural network, according to various embodiments, may include a plurality of nodes that mimic the operation of the human brain, a training mechanism that analyzes supplied information, and/or a personal data location engine for performing any one or more of the functions involving personal data as described herein, including, but not limited to, generating identity graphs and performing unstructured data redaction. The neural network may also perform any of the processing (e.g., execute any of the modules) described herein to locate, identify, retrieve, modify, and/or perform any other functions on linen inventory or restocking data. In various embodiments, each of the nodes may include one or more weighted input connections, one or more transfer functions that combine the inputs, and one or more output connections. In particular embodiments, the neural network is a variational autoencoder (AE) neural network, a denoising AE neural network, any other suitable neural network, or any combination thereof.

CONCLUSION

Many modifications and other embodiments of the invention will come to mind to one skilled in the art to which this invention pertains, having the benefit of the teaching presented in the foregoing descriptions and the associated drawings. For example, while it should be understood that the various embodiments above may be used within the context of managing linen within a healthcare facility (e.g., a hospital or clinic) or other facility (e.g., a hotel), it should be understood that the above systems and methods may be used to manage inventory levels of other types of items. Accordingly, it should be understood that the invention is not to be limited to the specific embodiments disclosed and that modifications and other embodiments are intended to be included within the scope of the appended claims. Although specific terms are employed herein, they are used in a generic and descriptive sense only and not for the purposes of limitation.

What is claimed:

1. A system for managing linen inventory, the system comprising:

a plurality of computerized smart bins that each comprise:

(1) at least one smart bin computer processor;

(2) memory that is operatively coupled to the at least one smart bin computer processor;

(3) at least one weight sensor that is adapted to measure a weight of linen items within the smart bin, and that is adapted to communicate with the at least one smart bin computer processor; and (4) at least one communications interface for communicating information from the at least one smart bin computer processor to a human user, wherein:

at least one of the plurality of computerized smart bins is substantially in the shape of a substantially hollow cuboid, wherein:

the substantially bollow cuboid comprises:

a substantially rectangular bottom platform;

a substantially planar, rectangular back wall that extends upwardly from a rear side of the bottom platform;

two substantially planar, substantially rectangular co-facing sidewalls that extend upwardly from respective sides of the bottom platform so that the back wall and side walls form a continuous, substantially U-shaped wall that extends upwardly from a portion of the perimeter of the bottom platform:

a substantially planar top portion that extends between respective tops of the sidewalls and that at least substantially extends from a rear of the substantially hollow cuboid to a front of the substantially hollow cuboid; and a substantially planar partial front wall portion comprising a first rectangular wall portion adjacent a first sidewall and a second rectangular portion adjacent a second sidewall and offset from the first rectangular portion, each of the first rectangular portion and the second rectangular portion extending upwardly from a front side of the bottom platform, and the substantially hollow cuboid defines:

an interior portion for storing the linen items; and a substantially T-shaped opening on the partial front wall portion through which a user may remove one or more linen items from the interior portion, the substantially T-shaped opening including:

a bottom, vertical portion that extends upward from the front side of the bottom platform between the first rectangular portion and the second rectangular portion; and an upper, horizontal portion that extends an entire width of the partial front wall portion and is defined by the two substantially planar, substantially rectangular co-facing sidewalls an upper edge of the bottom vertical portion, and respective upper edges of the first rectangular portion and the second rectangular portion; and each respective smart bin is adapted to weigh items within the respective smart bin, determine a current number of items stored within the respective smart bin based at least in part on the measured weight of items within the respective smart bin, and communicate, via the communications interface, an indication of a number of items that need to be added to, or removed from, the smart bin in order to meet a particular inventory objective.

2. The system of claim 1, wherein:

the system further comprises a smart cart; and at least two of the smart bins are disposed on the smart cart.

3. The system of claim 2, wherein the smart cart comprises:

at least one smart cart computer processor;

computer memory that is operatively coupled to the smart cart computer processor; and networking hardware that is adapted to facilitate communication between the smart cart and a central linen management server.

4. The system of claim 3, wherein each respective smart bin is connected to communicate with the at least one smart cart computer processor.

5. The system of claim 3, wherein each respective smart bin is connected to communicate with at least one other one of the plurality of computerized smart bins.

6. The system of claim 2, wherein the at least two of the smart bins are fixed with respect to the smart cart.

7. The system of claim 2, wherein the at least one weight sensor comprises four load cells, each respective load cell of the four load cells being disposed adjacent a respective corner of the bottom platform.

8. The system of claim 1, wherein the particular inventory objective is to maintain at least a particular number of linen items of a particular type of linen within the smart bin.

9. The system of claim 1, wherein at least one of the plurality of smart bins comprises a physical visual indicator on the inside of the smart bin that indicates the height of a stack of a certain type of item when the smart bin is loaded to PAR.

10. The system of claim 1, wherein:

the substantially hollow cuboid is a cube;

the substantially rectangular bottom platform is substantially square;

the substantially planar, rectangular back wall is substantially square;

the two substantially planar substantially rectangular co-facing sidewalls are substantially square;

the substantially planar top portion is substantially square.

11. A system for managing linen inventory, the system comprising:

a plurality of computerized smart bins that each comprise:

(1) at least one smart bin computer processor;

(2) memory that is operatively coupled to the at least one smart bin computer processor;

(3) at least one linen item sensor that is adapted to determine a quantity of linen items within the respective smart bin; and (4) at least one communications interface for communicating information from the at least one smart bin computer processor to a human user, wherein:

at least one of the plurality of computerized smart bins is substantially in the shape of a substantially hollow cuboid defining:

an interior portion for storing the linen items; and a front face comprising a first rectangular portion and a second rectangular portion offset form the first rectangular portion and defining a substantially T-shaped opening through which a user may remove one or more linen items from the interior portion, the substantially T-shaped opening having a bottom, vertical portion that extends upward from a base of the substantially hollow cuboid between the first rectangular portion and the second rectangular portion; and an upper, horizontal portion that extends a width of the front face and is defined by an upper edge of the bottom, vertical portion and respective upper edges of the first rectangular portion and the second rectangular portion; and each respective smart bin is adapted to use the at least one linen item sensor to determine a quantity of linen items within the respective smart bin and communicate, via the communications interface, an indication of a number of items that need to be added to, or removed from, the smart bin in order to meet a particular inventory objective.

12. The system of claim 11, wherein the smart cart comprises:

at least one smart cart computer processor;

computer memory that is operatively coupled to the smart cart computer processor; and networking hardware that is adapted to facilitate communication between the smart cart and a central linen management server.

13. The system of claim 12, wherein each respective smart bin is connected to communicate with the at least one smart cart computer processor.

14. The system of claim 13, wherein each respective smart bin is connected to communicate with at least one other one of the plurality of computerized smart bins.

15. The system of claim 11, wherein the particular inventory objective is to maintain at least a particular number of linen items of a particular type of linen within the smart bin.

16. The system of claim 11, wherein at least one of the plurality of smart bins comprises a physical visual indicator on the inside of the smart bin that indicates the height of a stack of a certain type of item when the smart bin is loaded to PAR.

17. The system of claim 11, wherein the linen item sensor is selected from a group consisting of: a scale, a camera, a light sensor, and an audio-based item sensor.

18. A method of managing linen inventory, the method comprising:

providing a plurality of computerized smart bins that each comprise:

(1) at least one smart bin computer processor;

(2) memory that is operatively coupled to the at least one smart bin computer processor;

(3) at least one weight sensor that is adapted to measure a weight of linen items within the smart bin, and that is adapted to communicate with the at least one smart bin computer processor; and (4) at least one communications interface for communicating information from the at least one smart bin computer processor to a human user, wherein:

at least one of the plurality of computerized smart bins is substantially in the shape of a substantially hollow cuboid, wherein, the substantially hollow cuboid comprises:

a substantially rectangular bottom platform;

a substantially planar, rectangular back wall that extends upwardly from a rear side of the bottom platform;

two substantially planar, substantially rectangular co-facing sidewalls that extend upwardly from respective sides of the bottom platform so that the back wall and side walls form a continuous, substantially U-shaped wall that extends upwardly from a portion of the perimeter of the bottom platform;

a substantially planar top portion that extends between respective tops of the sidewalls and that at least substantially extends from a rear of the substantially hollow cuboid to a front of the substantially hollow cuboid; and a substantially planar partial front wall portion comprising a first rectangular wall portion adjacent a first sidewall and a second rectangular portion adjacent a second sidewall and offset from the first rectangular portion, each of the first rectangular portion and the second rectangular portion extending upwardly from a front side of the bottom platform; and the substantially hollow cuboid defines:

an interior portion for storing the linen items; and a substantially T-shaped opening in the partial front wall portion through which a user may remove one or more linen items from the interior portion the substantially T-shaped opening including:

a bottom, vertical portion that extends upward from the front side of the bottom platform between the first rectangular portion and the second rectangular portion; and an upper, horizontal portion that extends an entire width of the partial front wall portion and is defined by the two substantially planar, substantially rectangular co-facing sidewalls, an upper edge of the bottom vertical portion, and respective upper edges of the first rectangular portion and the second rectangular portion; and each respective smart bin is adapted to weigh items within the respective smart bin, determine a current number of items stored within the respective smart bin based on the measured weight of items within the respective smart bin, and communicate, via the communications interface, an indication of a number of items that need to be added to, or removed from, the smart bin in order to meet a particular inventory objective;

using the plurality of smart bins to manage the inventory of linen items within a facility;

placing a folded stack of the linen items in the at least one of the plurality of computerized smart bins; and removing at least a portion of the folded stack of linen items from the at least one of the plurality of computerized smart bins by grasping the portion of the folded stack of linen items through the bottom, vertical portion of the substantially T-shaped opening, lifting the portion of the folded stack of linen items, and removing the portion of the stack of linen items through the upper. horizontal portion of the substantially T-shaped opening.

19. The method of claim 18, wherein the facility is a healthcare facility.

20. The method of claim 18, wherein:

the system further comprises a smart cart; and at least two of the smart bins are disposed on the smart cart.

* * * * *